United States Patent [19]

Zaugg et al.

[11] 4,018,777
[45] Apr. 19, 1977

[54] 2-SUBSTITUTED-5-ALKYL RESORCINOLS

[75] Inventors: Harold Elmer Zaugg, Lake Forest; Cheuk Man Lee, Libertyville; Raymond John Michaels, Mundelein; Nicholas Peter Plotnikoff, Lake Bluff, all of Ill.

[73] Assignee: Abbott Laboratories, North Chicago, Ill.

[22] Filed: Nov. 14, 1975

[21] Appl. No.: 632,126

[52] U.S. Cl. .................... 260/295.5 R; 260/295 T; 260/297 R; 260/343.2 R; 260/479 R; 260/612 D; 424/263

[51] Int. Cl.² .............. C07D 213/55; C07D 213/30

[58] Field of Search ................ 260/295.5 R, 297 R

[56] References Cited

UNITED STATES PATENTS 3,901,926  8/1975  Winn et al. ................... 260/297 T

OTHER PUBLICATIONS

Karrer, Organic Chemistry, 4th English Edit., p. 928, Elsevier Publ. Co., (N.Y.), 1950.

Primary Examiner—Alan L. Rotman
Attorney, Agent, or Firm—Vincent A. Mallare; Robert L. Niblack

[57] ABSTRACT

Covers 2-substituted-5-alkyl resorcinols represented by the formula

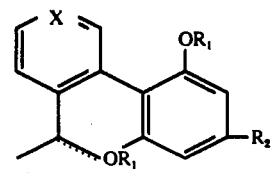

wherein $R_1$ is hydrogen or lower-alkanoyl; $R_2$ is a straight or branched chain alkyl of 1 to 20 carbon atoms; and X is nitrogen or C-methyl.

The compounds of this invention are useful as tranquilizers, analgesics, sedative-hypnotics and anticonvulsants.

13 Claims, No Drawings

2-SUBSTITUTED-5-ALKYL RESORCINOLS

DETAILED DESCRIPTION OF THE INVENTION

This invention relates to resorcinols and more particularly to 2-substituted-5-alkyl resorcinols represented by the formula

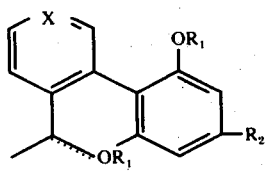

wherein $R_1$ is hydrogen or lower-alkanoyl; $R_2$ is a straight or branched chain alkyl of 1 to 20 carbon atoms; and X is nitrogen or C-methyl.

As used herein, the term "lower-alkanoyl" means saturated, monovalent, aliphatic radicals, derived from a monocarboxylic acid, inducing straight or branched chain radicals, of from 2 to 6 carbon atoms, as illustrated by, but not limited to acetyl, propionyl, α-methylpropionyl, butyryl, hexanoyl, and the like.

The term "alkyl" as used herein, means saturated monovalent, aliphatic radicals, including straight and branched chain radicals having 1 to 20 carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl, and the like.

The present resorcinols are prepared according to the following reaction scheme:

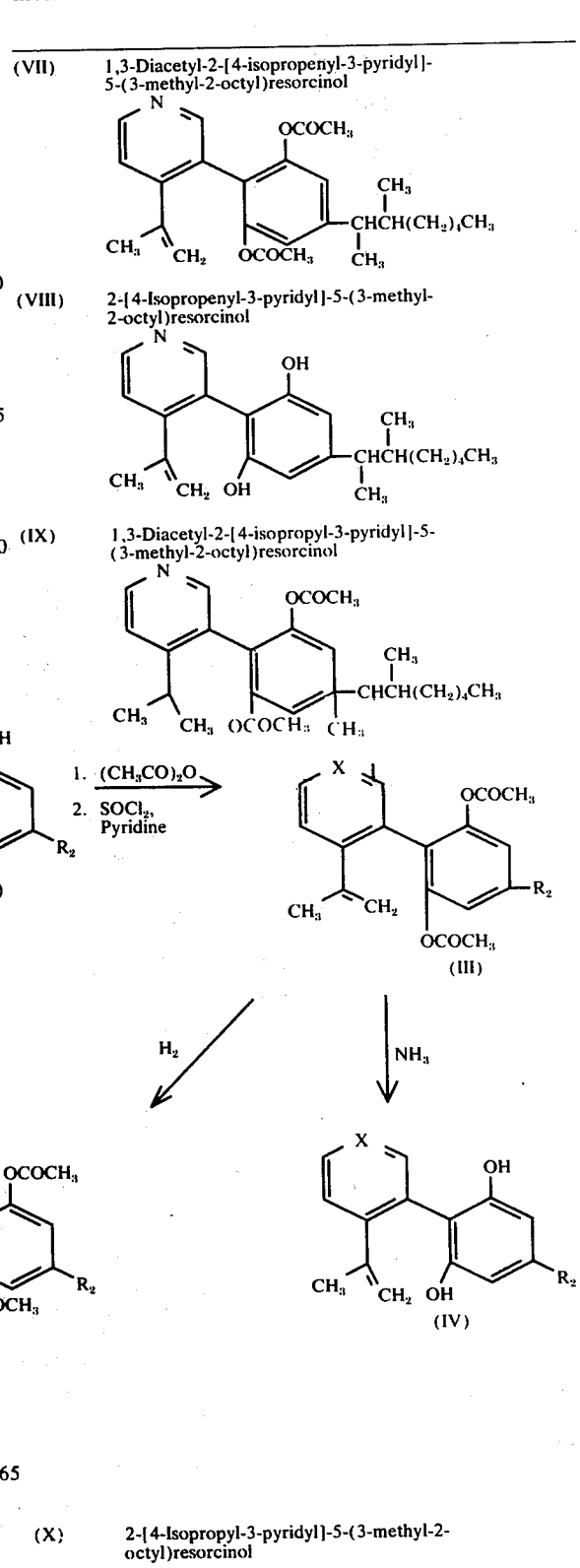

The benzopyranones (I) are allowed to react with methyl magnesium bromide in tetrahydrofuran to form the alcohols (II) which are treated with acetic anhydride in pyridine to yield the diacetyl derivatives, followed by dehydration with thionyl chloride in pyridine at −10° to 0° to give the isopropenyl derivatives (III). Treatment of (III) with liquid ammonia in a high pressure bomb at room temperature yields the resorcinols (IV). Hydrogenation of the isopropenyl derivatives (III) with 5% palladium on carbon in ethyl acetate yields the isopropyl derivatives (V) which are treated with liquid ammonia in a high pressure bomb at room temperature to give the deacetylated derivatives (VI).

The present compounds which can be produced by the general scheme, as illustrated and described above, include:

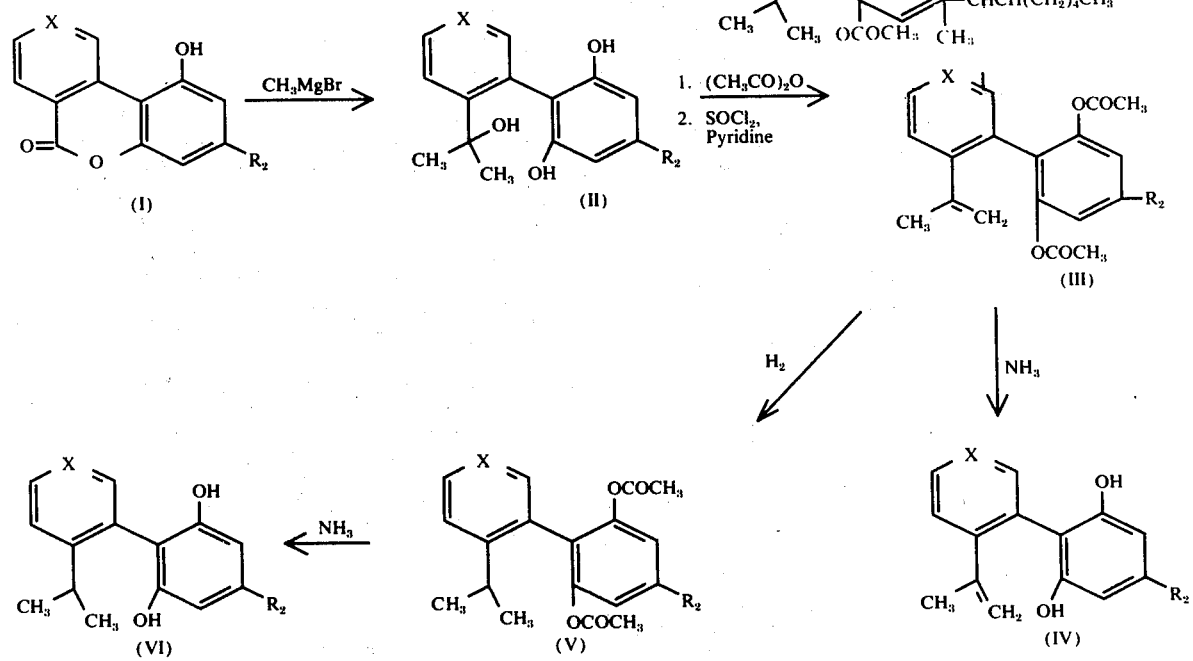

(VII)  1,3-Diacetyl-2-[4-isopropenyl-3-pyridyl]-5-(3-methyl-2-octyl)resorcinol (VIII) 2-[4-Isopropenyl-3-pyridyl]-5-(3-methyl-2-octyl)resorcinol (IX) 1,3-Diacetyl-2-[4-isopropyl-3-pyridyl]-5-(3-methyl-2-octyl)resorcinol (X) 2-[4-Isopropyl-3-pyridyl]-5-(3-methyl-2-octyl)resorcinol

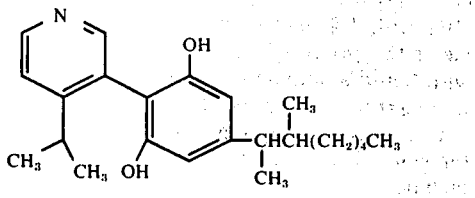

(XI) 1,3-Diacetyl-2-[(2-isopropenyl-5-methyl)phenyl]-5-(3-methyl-2-octyl)resorcinol

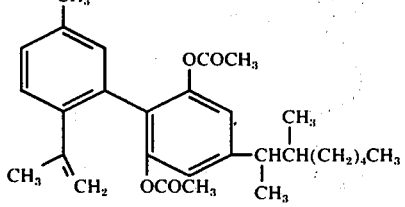

(XII) 2-[(2-Isopropyl-5-methyl)phenyl]-5-(3-methyl-2-octyl)resorcinol

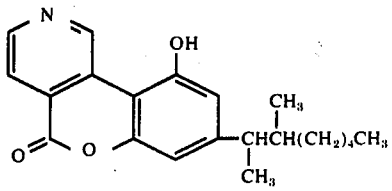

The compounds of this invention are useful as analgesic agents, tranquilizers, sedative-hypnotics and anticonvulsants. The compounds are effective at dosages generally of from 1 to 10 mg./kg. of body weight daily. The analgesic activity was established in the standard mouse writhing test [Whittle, Brit. J. Pharmacol., 22, 296 (1964)] and confirmed in the hot plate assay [Woolfe, G. and McDonald, A. J., J. Pharmacol, Exper. Therap., 80, 300 (1944)] and the rat tail flick test.

The following examples further illustrate and describe the present invention:

EXAMPLE 1

10-Hydroxy-8-(3-Methyl-2-Octyl)-5-Oxo-5H-[1]Benzopyrano[4,3-c]Pyridine

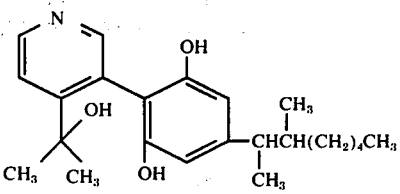

A mixture of 3.42 g. of 2-benzyl-10-hydroxy-8-(3-methyl-2-octyl)-5-oxo-1,2,3,4-tetrahydro-5H-[1]benzopyrano[4,3-c]pyridine, 1.0 g. of 10% palladium on carbon, and 120 ml. of xylene was stirred and refluxed for 23 hours. The mixture was filtered to remove the catalyst and the filtrate was evaporated to dryness in vacuo. The residue was recrystallized from acetonitrile to yield the pure product; m.p. 122°–123°.

Analysis Calcd. for: $C_{21}H_{25}NO_3$: C, 74.31; H, 7.42; N, 4.13 Found: C, 74.08; H, 7.36; N, 3.98

EXAMPLE 2

2-{4-[(1-Hydroxy-1-Methyl)Ethyl]-3-Pyridyl}-5-(3-Methyl-2-Octyl)Resorcinol

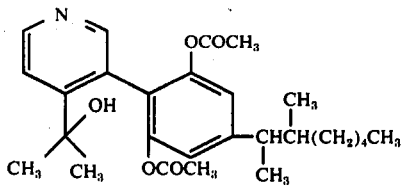

A solution of 16.97 g. (0.05 mole) of 10-hydroxy-8-(3-methyl-2-octyl)-5-oxo-5H-[1]benzopyrano[4,3-c]pyridine in 125 ml. of tetrahydrofuran was added gradually to a stirred solution of 125 ml. of 3M methyl magnesium bromide in ether and 125 ml. of tetrahydrofuran so that the solution was refluxed gently. After the addition, the reaction mixture was heated under reflux for 1½ hours and, on cooling, was decomposed with 200 ml. of saturated ammonium chloride solution and was extracted twice with tetrahydrofuran. The tetrahydrofuran extracts were dried over anhydrous sodium sulfate and evaporated in vacuo to yield the product; m.p. 82°–87°.

EXAMPLE 3

1,3-Diacetyl-2-{4-[(1-Hydroxy-1-Methyl)Ethyl]-3-Pyridyl}-5-(3-Methyl-2-Octyl)Resorcinol

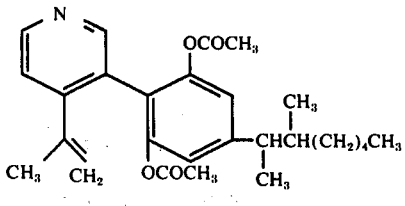

Acetic anhydride (7.65 g.) was added dropwise to a stirred solution of 9.73 g. of 2-{4-[(1-hydroxy-1-methyl)ethyl]-3-pyridyl}-5-(3-methyl-2-octyl)resorcinol in 40 ml. of dry pyridine, cooled in an ice bath. The mixture was stirred at ice bath temperature for 1 hour and then at room temperature overnight, and was concentrated in vacuo. The residue was poured into 300 ml. of ice water and the gummy material was taken up in ether. The ether solution was washed twice with water, dried over anhydrous sodium sulfate, and evaporated in vacuo to give the product, which was used for the next step without further purification.

EXAMPLE 4

1,3-Diacetyl-2-[4-Isopropenyl-3-Pyridyl]-5-(3-Methyl-2-Octyl)Resorcinol

Thionyl chloride (5 ml.) was added dropwise to a stirred solution of 1.27 g. of 1,3-diacetyl-2-{4-[1- hydroxy-1-methyl)ethyl]-3-pyridyl}-5-(3-methyl-2-octyl)resorcinol in 40 ml. of pyridine, cooled in an ice-salt bath at −10°. The mixture was stirred and the temperature was allowed to rise to 0° within 1½ hours. The mixture was poured into ice water and was extracted with ether. The ether extracts were washed with water, dried over anhydrous sodium sulfate, and evaporated in vacuo. The residue was chromatographed on a Florisil column (60–100 mesh) using graded methanol/benzene solvent mixtures to give the pure product.

Analysis Calcd. for: $C_{27}H_{35}NO_4$: C, 74.11; H, 8.06; N, 3.20; Found: C, 74.19; H, 8.02; N, 3.23.

EXAMPLE 5

2-[4-Isopropenyl-3-Pyridyl]-5-(3-Methyl-2-Octyl)Resorcinol

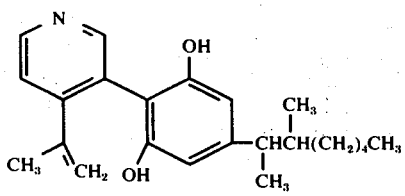

A solution of 4.37 g. of 1,3-diacetyl-2-[4-isopropenyl-3-pyridyl]-5-(3-methyl-2-octyl)resorcinol in 50 ml. of toluene was placed in a high pressure bomb with 40 ml. of liquid ammonia. The mixture was shaken at room temperature overnight. The excess ammonia was allowed to escape; the residue was triturated with water and extracted with chloroform. The chloroform extracts were washed twice with water, dried over anhydrous sodium sulfate, and evaporated in vacuo. The residue was recrystallized from ether-petroleum ether (30°–60°) to yield the pure product; m.p. 128°–129°.

Analysis Calcd. for: $C_{23}H_{31}NO_2$: C, 78.14; H, 8.84; N, 3.97; Found: C, 78.43; H, 8.98; N, 3.99.

EXAMPLE 6

1,3-Diacetyl-2-[4-Isopropyl-3-Pyridyl]-5-(3-Methyl-2-Octyl)Resorcinol

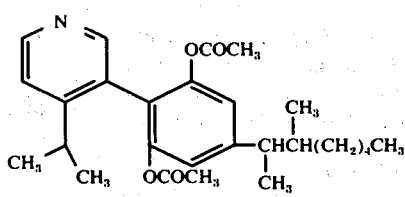

A solution of 6.0 g. of 1,3-diacetyl-2-[4-isopropenyl-3-pyridyl]-5-(3-methyl-2-octyl)resorcinol in 200 ml. of ethyl acetate with 1.2 g. of 5% palladium on carbon was hydrogenated in a Parr apparatus for 1½ hours. The solution was filtered and 1.2 g. of 5% palladium on carbon was added and the mixture was hydrogenated for 4 hours. After removal of the catalyst, the filtrate was evaporated in vacuo to yield the pure product.

Analysis Calcd. for: $C_{27}H_{37}NO_4$: C, 73.78; H, 8.52; N, 3.20; Found: C, 73.47; H, 8.59; N, 3.01.

EXAMPLE 7

2-[4-Isopropyl-3-Pyridyl]-5-(3-Methyl-2-Octyl)Resorcinol

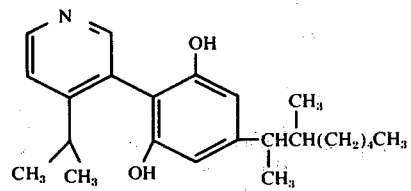

2-[4-Isopropyl-3-pyridyl]-5-(3-methyl-2-octyl)resorcinol was prepared by treating 1,3-diacetyl-2-[4-isopropyl-3-pyridyl]-5-(3-methyl-2-octyl)resorcinol with ammonia according to the procedure of Example 5.

EXAMPLE 8

1-Hydroxy-9-Methyl-3-(3-Methyl-2-Octyl)-6-Oxo-6H-Dibenzo[b][d]Pyran

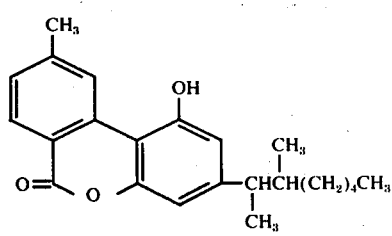

A mixture of 8.4 g. of 1-hydroxy-9-methyl-3-(3-methyl-2-octyl)-6-oxo-7,8,9,10-tetrahydro-6H-dibenzo[b][d]-pyran and 2.4 g. of sulfur was heated in an oil bath at 225°–260° for ½ hour. After cooling, 100 ml. of ether was added to the residue and the ether solution was filtered to remove insoluble material. The filtrate was concentrated in vacuo to yield 7.9 g. of amorphous solid; m.p. 80°–85°.

EXAMPLE 9

2-{2-[(1-Hydroxy-1-Methyl)Ethyl]-5-Methylphenyl}-5-(3-Methyl-2-Octyl)Resorcinol

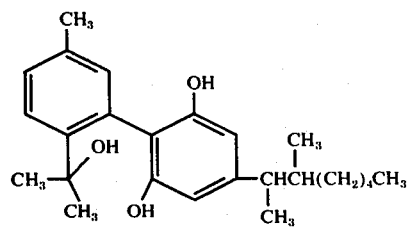

2-{2-[(1-Hydroxy-1-methyl)ethyl]-5-methylphenyl}-5-(3-methyl-2-octyl)resorcinol was prepared by reaction of 1-hydroxy-9-methyl-3-(3-methyl-2-octyl)-6-oxo-6H-dibenzo[b][d]pyran with methyl magnesium bromide and decomposing the complex with aqueous sodium carbonate according to the procedure of Example 2.

EXAMPLE 10

1,3-Diacetyl-2-{2-[(1-Hydroxy-1-Methyl)Ethyl]-5-Methylphenyl}-5-(3-Methyl-2-Octyl)Resorcinol

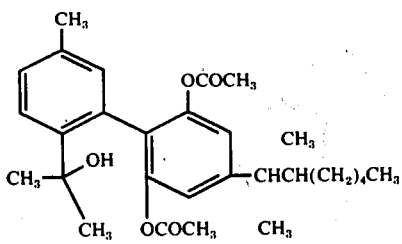

1,3-Diacetyl-2-{2-[(1-hydroxy-1-methyl)ethyl]-5-methylphenyl}-5-(3-methyl-2-octyl)resorcinol was prepared by treating 2-{2-[(1-hydroxy-1-methyl)ethyl]-5-methylphenyl}-5-(3-methyl-2-octyl)resorcinol with acetic anhydride in pyridine according to the method of Example 3.

EXAMPLE 11

1,3-Diacetyl-2-[(2-isopropenyl-5-methyl)phenyl]-5-(3-methyl-2-octyl)Resorcinol

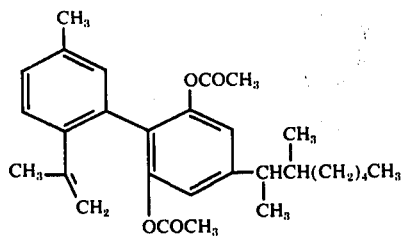

1,3-Diacetyl-2-[(2-isopropenyl-5-methyl)phenyl]-5-(3-methyl-2-octyl)resorcinol was prepared by reaction of 1,3-diacetyl-2-{2-[(1-hydroxy-1-methyl)ethyl]-5-methylphenyl}-5-(3-methyl-2-octyl)resorcinol with thionyl chloride and pyridine according to the procedure of Example 4.

Analysis Calcd. for: $C_{29}H_{38}O_4$: C, 77.30; H, 8.50; O, 14.20; Found: C, 76.82; H, 8.60; O, 13.67.

EXAMPLE 12

1,3-Diacetyl-2-[(2-isopropyl-5-methyl)phenyl]-5-(3-methyl-2-octyl)Resorcinol

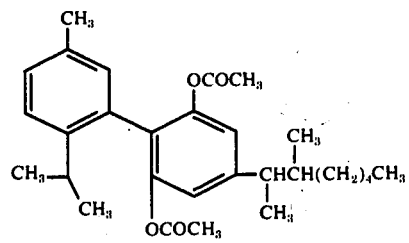

A solution of 2.5 g. of 1,3-diacetyl-2-[(2-isopropenyl-5-methyl)phenyl]-5-(3-methyl-2-octyl)resorcinol in 100 ml. of deoxygenated benzene with 1.0 g. of tristriphenyl phosphine rhodium chloride was hydrogenated under three atmospheric pressures at room temperature overnight. The solution was concentrated to dryness in vacuo; the residue was dissolved in ether and the ether solution was passed through a Florisil column to remove the catalyst. The eluant was concentrated in vacuo to yield the product.

EXAMPLE 13

2-[(2-Isopropyl-5-Methyl)Phenyl]-5-(3-Methyl-2-Octyl)Resorcinol

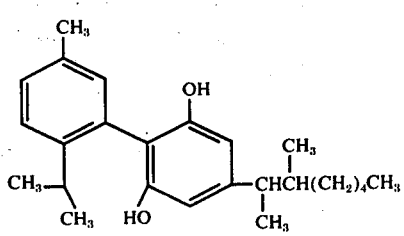

2-[(2-Isopropyl-5-methyl)phenyl]-5-(3-methyl-2-octyl)resorcinol was prepared by treating 1,3-diacetyl-2-[(2-isopropyl-5-methyl)phenyl]-5-(3-methyl-2-octyl)resorcinol with ammonia according to the procedure of Example 7, and purified by chromatography on a Florisil column (60–100 Mesh) using graded ether/petroleum ether (30°–60°) solvent mixtures.

Analysis Calcd. for: $C_{25}H_{36}O_2$: C, 81.47; H, 9.85; O, 8.68; Found: C, 80.91; H, 9.85; O, 8.99.

EXAMPLE 14

There have been several tests made using the compounds of the present invention to determine their utility and efficacy as antipsychotic, analgesic and anticonvulsant agents. The tests using the compounds of the present invention are described below, and the results of the tests are recorded below in Table I.

Test 1

Antipsychotic Activity (Rat Desoxyn Antagonism)

Antipsychotic activity (*Desoxyn antagonism*) was evaluated in motor activity chambers equipped with photocells. Groups of nine rats were given the compound orally one hour before the test and then administered methamphetamine (Desoxyn) 3 mg./kg. sc, and placed in the chamber. Changes in motor activity were recorded as counts from the photocells and are compared to Desoxyn treated controls.

Test 2

Analgesic Activity

In testing for the analgesic effect of the present compounds, the acetic acid writhing test was made as that described by [B. A. Whittle, *Brit. J. Pharmacol* 22, 246 (1964)]. Groups of Swiss-Webster female mice were given oral doses of the drug or control vehicle. The use of the intravenous dye was eliminated. One hour later they were given 0.4 ml. of 0.5% HOAc intraperitoneally. The number of writhes occurring in 20 minutes were counted starting 5 minutes after the injection of HOAc. Analgesic activity was reported as percent inhibition of writhing vs. controls or as $ED_{50\%}$.

In testing for analgesic activity by the rat tail flick method described by [F. E. D'Amour and D. L. Smith, *J Pharmcol. Exp. Ther.* 72, 74 (1941)], the method was modified as follows. Groups of male Sprague-Dawley rats weighing 140–170 g. are prepared by blackening their tails with India ink. Radiant heat is focused on their tails and adjusted so that the normal pain threshholds (time in seconds until an escape response or tail flick occurs) are in the range of 8 to 10 seconds. This is followed by oral administration of the test compound and hourly measurements of the animals' pain threshholds. The analgesic effects are listed in Table I as percent increase over initial pain threshhold 2 hours after dosing, or $ED_{50}$'s.

Test 3

Audiogenic Seizure Test (Mouse)

Male O'Grady strain mice (14 to 16 g.) especially bred for susceptibility to audiogenic seizures were used as subjects. The audiogenic apparatus consisted of a wooden box enclosing a metal container with two doorbells attached to the upper section. After drug administration the animals were placed in the audiogenic chamber and the bells activated for one minute and the animals were observed for convulsion. [Ref: N. P. Plotnikoff and D. M. Green, *J, Pharmacol. Exp. Ther.*, 119, 294 (1957)].

TABLE I

| | Antipsychotic Activity (Rat Desoxyn Antagonism) | Analgesic Activity | Anticonvulsant Activity Audiogenic Seizure 1 hr., % protection |
|---|---|---|---|
| Compound (VII) Example 4 | 10 mg./kg. - 66% | RTF: 23% at 20 mg./kg. | $ED_{50}$ 9 mg./kg. (est.) |
| Compound (VIII) Example 5 | Inactive | RTF: 59% at 40 mg./kg. | 100 mg./kg. 100% |
| Compound (IX) Example 6 | | W(PO): 30% at 80 mg./kg. RTF: 20% at 40 mg./kg. | |
| Compound (X) Example 7 | | W(PO): $ED_{50}$ = 44 mg./kg. RTF: 53% at 40 mg./kg. | 100 mg./kg. 60% |
| Compound (XI) Example 11 | 10 mg./kg. - 55% | W(PO) 40-50% at 10-40 mg./kg. | 100 mg./kg. = 70% |
| Compound (XII) Example 13 | 10 mg./kg. - 77% | W(PO): 47% at 40 mg./kg. RTF: 45% at 22 mg./kg. | 100 mg./kg. = 60% |

The present invention includes within its scope, pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as in normal practice, additional substances other than inert diluents, e.g., lubricating agents such as magnesium stearates and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents, and sweetening, flavoring and perfuming agents.

Preparations according to this invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ester oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions or by heating the compositions. They can also be manufactured in the form of sterile solid compositions which can be dissolved in sterile water or some other sterile injectable medium immediately before use.

Compositions for rectal administration are suppositories which may contain in addition to the active substance, excipients such as cocoa butter or a suppository wax.

The dosage of active ingredients in the compositions of this invention may be varied; however, it is necessary that the amount of the active ingredient shall be such that a suitable dosage form is obtained. The selected dosage depends upon the desired therapeutic effect, on the route of administration and on the duration of the treatment.

We claim:

1. A 2-substituted -5-alkyl resorcinol having one of the following formulas

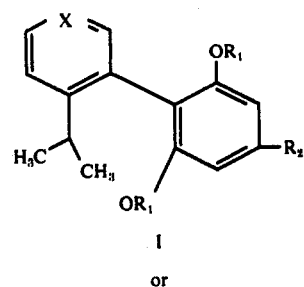

I or

-continued

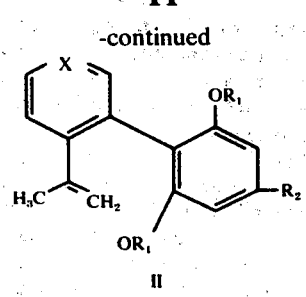

II wherein $R_1$ is hydrogen or lower-alkanoyl; $R_2$ is a straight or branched chain alkyl of 1 to 9 carbon atoms; and X is nitrogen.

2. A compound according to claim 1, wherein $R_1$ is hydrogen, $R_2$ is alkyl; and X is N.

3. A compound in accordance with claim 2, 2-{[(1-hydroxy-1-methyl)ethyl]-3-pyridyl}-5-(3-methyl-2-octyl)resorcinol.

4. A compound according to claim 1, wherein $R_1$ is —C(O)CH$_3$, $R_2$ is $C_9$ alkyl, and X is N.

5. A compound according to claim 4, 1,3-diacetyl-2-{4-[(1-hydroxy-1-methyl)ethyl]-3-pyridyl}-5-(3-methyl-2-octyl)resorcinol.

6. A compound according to claim 1, wherein $R_1$ is —C(O)CH$_3$, $R_2$ is a $C_9$ alkyl and X is N.

7. A compound according to claim 6, 1,3-diacetyl-2-[4-isopropenyl-3-pyridyl]-5-(3-methyl-2-octyl)resorcinol.

8. A compound in accordance with claim 1, wherein each $R_1$ is H, $R_2$ is a $C_9$ alkyl and X is N.

9. A compound in accordance with claim 8, 2-[4-isopropenyl-3-pyridyl]-5-(3-methyl-2-octyl)resorcinol.

10. A compound in accordance with claim 1, wherein each $R_1$ is C(O)CH$_3$, $R_2$ is a $C_9$ alkyl and X is N.

11. A compound in accordance with claim 10, 1,3-diacetyl-2-[4-isopropyl-3-pyridyl]-5-(3-methyl-2-octyl)resorcinol.

12. A compound according to claim 1, wherein each $R_1$ is H, $R_2$ is a $C_9$ alkyl and X is N.

13. A compound according to claim 12, 2-[4-isopropyl-3-pyridyl]-5-(3-methyl-2-octyl)resorcinol.

* * * * *